(12) United States Patent
Ogawa et al.

(10) Patent No.: US 10,814,527 B2
(45) Date of Patent: Oct. 27, 2020

(54) METHOD OF PRODUCING TRANSDERMAL ABSORPTION SHEET

(71) Applicant: FUJIFILM Corporation, Tokyo (JP)

(72) Inventors: Shotaro Ogawa, Kanagawa (JP); Kenichiro Tamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 294 days.

(21) Appl. No.: 15/940,985

(22) Filed: Mar. 30, 2018

(65) Prior Publication Data

US 2018/0222088 A1    Aug. 9, 2018

Related U.S. Application Data

(63) Continuation of application No. PCT/JP2016/078556, filed on Sep. 28, 2016.

(30) Foreign Application Priority Data

Oct. 6, 2015 (JP) .................................. 2015-198402
Feb. 9, 2016 (JP) .................................. 2016-022835

(51) Int. Cl.
*B29C 33/38* (2006.01)
*B29C 33/40* (2006.01)
(Continued)

(52) U.S. Cl.
CPC ........ *B29C 33/3842* (2013.01); *A61K 9/0021* (2013.01); *A61K 9/703* (2013.01);
(Continued)

(58) Field of Classification Search
CPC .............. B29C 33/3842; B29C 33/424; B29C 33/3857; B29C 33/40; B29C 41/36;
(Continued)

(56) References Cited

U.S. PATENT DOCUMENTS 6,716,332 B1    4/2004    Yoshioka et al.
6,746,590 B2    6/2004    Zhang et al.
(Continued)

FOREIGN PATENT DOCUMENTS

JP    H04-238129    8/1992
JP    H08-129782    5/1996
(Continued)

OTHER PUBLICATIONS

"International Search Report (Form PCT/ISA/210) of PCT/JP2016/078556", dated Nov. 8, 2016, with English translation thereof, pp. 1-4.
(Continued)

*Primary Examiner* — Abbas Rashid
*Assistant Examiner* — S. Behrooz Ghorishi
(74) *Attorney, Agent, or Firm* — JCIPRNET

(57) ABSTRACT

Provided is a method of producing a transdermal absorption sheet using an electroforming mold. A method of manufacturing an electroforming mold includes preparing a mold which is a matrix having a recessed pattern, immersing the mold in a degassed pretreatment liquid stored in a pretreatment liquid tank, then applying ultrasound waves generated from an ultrasound oscillator to the recessed pattern of the mold, and filling recessed portions constituting the recessed pattern with the pretreatment liquid. By immersing the mold in an electroforming tank and performing an electroforming treatment, an electroforming mold is manufactured. A mold having a recessed pattern is manufactured from the electroforming mold and a transdermal absorption sheet is produced using the mold.

10 Claims, 14 Drawing Sheets

(51) Int. Cl.

| | |
|---|---|
| *B29C 41/02* | (2006.01) |
| *B29C 41/42* | (2006.01) |
| *C25D 1/10* | (2006.01) |
| *A61K 47/36* | (2006.01) |
| *A61K 38/38* | (2006.01) |
| *A61K 9/70* | (2006.01) |
| *C25D 21/04* | (2006.01) |
| *A61M 37/00* | (2006.01) |
| *A61K 9/00* | (2006.01) |
| *B29C 41/36* | (2006.01) |
| *C25D 17/10* | (2006.01) |
| *B29C 33/42* | (2006.01) |
| *B29C 39/02* | (2006.01) |
| *B29L 31/00* | (2006.01) |
| *B29K 105/00* | (2006.01) |
| *C25D 3/12* | (2006.01) |
| *C25D 17/02* | (2006.01) |

(52) U.S. Cl.
CPC ............ *A61K 38/385* (2013.01); *A61K 47/36* (2013.01); *A61M 37/00* (2013.01); *A61M 37/0015* (2013.01); *B29C 33/3857* (2013.01); *B29C 33/40* (2013.01); *B29C 33/424* (2013.01); *B29C 39/02* (2013.01); *B29C 41/02* (2013.01); *B29C 41/36* (2013.01); *B29C 41/42* (2013.01); *C25D 1/10* (2013.01); *C25D 17/10* (2013.01); *C25D 21/04* (2013.01); *B29K 2105/0035* (2013.01); *B29K 2105/0073* (2013.01); *B29L 2031/753* (2013.01); *B29L 2031/756* (2013.01); *B29L 2031/7544* (2013.01); *C25D 3/12* (2013.01); *C25D 17/02* (2013.01)

(58) Field of Classification Search
CPC ......... B29C 39/02; B29C 41/42; C25D 21/04; C25D 17/10; C25D 1/10; C25D 3/12; C25D 17/02; C25D 1/00; A61M 37/00; A61M 37/0015; A61M 2037/0053; A61K 9/0021; A61K 47/36; A61K 38/385; A61K 9/703; B29L 2031/7544; B29L 2031/756; B29L 2031/753; B29K 2105/0073; B29K 2105/0035

See application file for complete search history.

(56) References Cited

U.S. PATENT DOCUMENTS

| | | | |
|---|---|---|---|
| 7,118,664 B2 | | 10/2006 | Yoshioka et al. |
| 2003/0042145 A1 | * | 3/2003 | Zhang ............... C25D 5/18 205/148 |
| 2004/0159550 A1 | * | 8/2004 | Yoshioka ............ C23C 18/1605 205/98 |
| 2015/0238413 A1 | | 8/2015 | Mochizuki et al. |
| 2016/0082626 A1 | | 3/2016 | Kato et al. |

FOREIGN PATENT DOCUMENTS

| | | | | |
|---|---|---|---|---|
| JP | H08-180475 | | 7/1996 | |
| JP | H09-35337 | | 2/1997 | |
| JP | 2002038295 | | 2/2002 | |
| JP | 2004-288266 | | 10/2004 | |
| JP | 2009167497 | | 7/2009 | |
| JP | 2015136528 | | 7/2015 | |
| JP | 2015136528 A | * | 7/2015 | ........ A61M 37/0015 |
| KR | 20010033965 | | 4/2001 | |
| WO | 03020359 | | 3/2003 | |
| WO | 2014077242 | | 5/2014 | |
| WO | 2014196522 | | 12/2014 | |

OTHER PUBLICATIONS

"Written Opinion (Form PCT/ISA/237)", dated Nov. 8, 2016, with English translation thereof, pp. 1-7.
Office Action of China Counterpart Application, with English translation thereof, dated Jan. 3, 2019, pp. 1-17.
"Search Report of Europe Counterpart Application", dated Dec. 21, 2018, p. 1-p. 8.
"Office Action of Korea Counterpart Application", dated Aug. 8, 2019, with English translation thereof, pp. 1-10.
"Office Action of China Counterpart Application", dated Aug. 19, 2019, with English translation thereof, pp. 1-16.
"Decision of Rejection of China Counterpart Application", dated Dec. 30, 2019, with English translation thereof, p. 1-p. 14.

* cited by examiner

60

60

METHOD OF PRODUCING TRANSDERMAL ABSORPTION SHEET

CROSS-REFERENCE TO RELATED APPLICATIONS

The present application is a Continuation of PCT International Application No. PCT/JP2016/078556 filed on Sep. 28, 2016 claiming priorities under 35 U.S.C. § 119(a) to Japanese Patent Application No. 2015-198402 filed on Oct. 6, 2015 and Japanese Patent Application No. 2016-022835 filed on Feb. 9, 2016. Each of the above applications is hereby expressly incorporated by reference, in their entirety, into the present application.

BACKGROUND OF THE INVENTION

1. Field of the Invention

The present invention relates to a method of producing a transdermal absorption sheet.

2. Description of the Related Art

In recent years, as a new dosage form capable of administering drugs such as insulin, vaccines, and human growth hormones (hGHs) into the skin without pain, a micro-needle array has been known. A micro-needle array is formed by arranging biodegradable micro-needles containing a drug (also referred to as fine needles) in an array. By attaching the micro-needle array to the skin, each micro-needle is inserted into the skin and these micro-needles are absorbed into the skin so that the drug included in each micro-needle can be administered into the skin. The micro-needle array is also referred to as a transdermal absorption sheet.

In a method of producing a micro-needle array for the above-described medical use or beauty, a metal micro-needle array manufactured by machining is used as an original plate. A recessed mold which is a reverse type resin mold is manufactured using the manufactured micro-needle array original plate. Next, a micro-needle array for medical use or beauty is produced from the manufactured mold. For mass production of the micro-needle array for medical use or beauty, a large number of original plates are required. However, in a case where the original plate manufactured by machining (metal micro-needle array) is produced in large quantity, the number of operations for manufacturing the original plate is increased and thus the manufacturing cost for the original plate is increased.

Herein, it is considered that a mold is manufactured from the original plate and the original plate is duplicated by an electroforming method using the mold. In a case of using an electroforming method, a duplicated mold of the original plate can be effectively manufactured and thus it is possible to reduce the cost.

However, in a case where an electroforming treatment is performed by attaching a recessed mold to a cathode, gas (bubbles) may adhere to the recessed portions of the mold in some cases. There is a concern about cavities being generated inside the protruding portions of an electroformed film or defects being generated in the protruding portions of the electroformed film due to the gas in the recessed portions.

JP1992-238129A (JP-H04-238129A) discloses that the gas adhering to an original plate attached to a cathode is removed by applying ultrasound waves to an electroforming liquid.

SUMMARY OF THE INVENTION

However, only with the technique of applying ultrasound waves described in JP1992-238129A (JP-H04-238129A), it is difficult to fully remove the gas adhering to the original plate. In a case where gas is not fully removed, cavities and/or defects are generated in an electroforming mold. As a result, it is difficult to produce a transdermal absorption sheet using the electroforming mold.

The present invention is made in consideration of the above circumstances and an object thereof is to provide a method of producing a transdermal absorption sheet using an electroforming mold.

According to an aspect of the present invention, there is provided a method of producing a transdermal absorption sheet comprising: a preparation step of preparing a matrix having a needle-like recessed pattern; a filling step of immersing the matrix in a degassed pretreatment liquid stored in a pretreatment liquid tank and applying ultrasound waves generated from an ultrasound oscillator to the recessed pattern of the matrix to fill recessed portions constituting the recessed pattern with the pretreatment liquid; a taking-out step of taking out the matrix from the pretreatment liquid tank; a formation step of immersing the matrix in an electroforming liquid stored in an electroforming tank and performing an electroforming treatment to form a metal body on a surface of the matrix on which the recessed pattern is formed; a peeling-off step of peeling off the metal body from the matrix to obtain an electroforming mold having a protruding pattern having an inverted shape of the recessed pattern; a step of manufacturing a mold having a recessed pattern using the electroforming mold; and a step of filling the recessed pattern of the mold with a polymer solution including a drug and then drying the polymer solution to form a polymer sheet.

Preferably, the pretreatment liquid is water.

Preferably, the ultrasound oscillator and the surface of the matrix on which the recessed pattern is formed are arranged to face each other.

Preferably, the matrix is formed of a resin material.

Preferably, the resin material is a thermoplastic resin or an ultraviolet curable resin.

Preferably, a dissolved oxygen concentration of the degassed pretreatment liquid is 0.5 mg/L or less.

Preferably, the method of producing a transdermal absorption sheet further comprises providing a vacuum degassing device which is connected to the pretreatment liquid tank via a circulation flow passage, the degassed pretreatment liquid is prepared by circulating the pretreatment liquid between the pretreatment liquid tank and the vacuum degassing device.

Preferably, the step of manufacturing the mold includes manufacturing a resin mold having a recessed pattern having an inverted shape of the protruding pattern of the electroforming mold.

Preferably, the method of producing a transdermal absorption sheet further comprises a peeling-off step of peeling off the polymer sheet from the mold.

Preferably, the polymer solution includes a water-soluble material.

According to the present invention, it is possible to produce a transdermal absorption sheet using an electroforming mold.

DESCRIPTION OF THE PREFERRED EMBODIMENTS

Figure 1A:
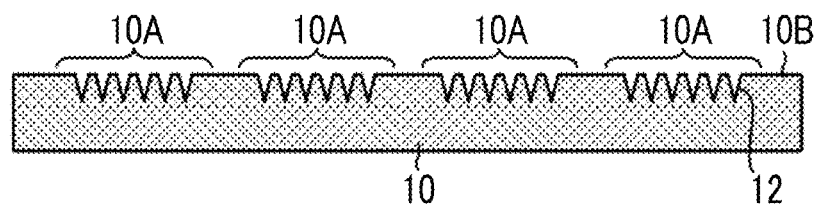
FIG. 1A is a step view showing a procedure of a method of manufacturing an electroforming mold.

Hereinafter, preferred embodiments of the present invention will be described with reference to the attached drawings. The present invention will be described using the following preferred embodiments. Modifications can be made by many methods without departing from the range of the present invention, and embodiments other than the embodiments can be used. Accordingly, all modifications within the range of the present invention are included in the range of the scope of the claims.

Herein, in the drawings, portions which are indicated by the same reference numeral are similar components having similar functions. In addition, in the present specification, in a case in which a numerical range is described using "to", numerical values for the upper limit and the lower limit which are represented by "to" are also included in the numerical range.

The preferred embodiments of the present invention will be described with reference to the attached drawings. FIGS. 1A to 4C are step views showing a procedure of a method of manufacturing an electroforming mold. FIG. 5 is a perspective view showing a mold which is a matrix.

FIG. 1A shows a preparation step of preparing a mold 10 which becomes a matrix. As shown in FIGS. 1A and 5, the mold 10 has needle-like recessed patterns 10A (hereinafter, simply also referred to as recessed patterns 10A) formed on a surface 10B (or one surface) side. The recessed pattern 10A has an inverted shape of a protruding pattern of an electroforming mold to be manufactured (or a protruding pattern of a transdermal absorption sheet to be manufactured).

The needle-like recessed pattern 10A is constituted of needle-like recessed portions 12 extending from the surface 10B of the mold 10 to the other surface and refers to a state in which the recessed portions 12 are arranged on the surface 10B side of the mold 10. The number of recessed portions, the arrangement of the recessed portions, the depth of the recessed portion, and the like are not limited. Here, the term "needle-like" means a shape which is tapered in a depth direction from the surface 10B to the other surface. For example, a conical shape, a combination of a columnar shape and a conical shape, a combination of a frustum shape and a conical shape, and the like may be adopted. In addition, a ratio of depth with respect to opening length (aspect ratio) of the recessed portion is 1.2 to 8.0.

Since the recessed pattern 10A has an inverted shape of a protruding pattern of an electroforming mold to be manufactured, the size of each recessed portion of the recessed pattern 10A, the number of recessed portions, and the arrangement of the recessed portions are basically the same as those of the protruding pattern of the electroforming mold. As shown in FIGS. 1A and 5, 4×4 recessed patterns 10A are formed on the surface 10B side of the mold 10.

Figure 1B:
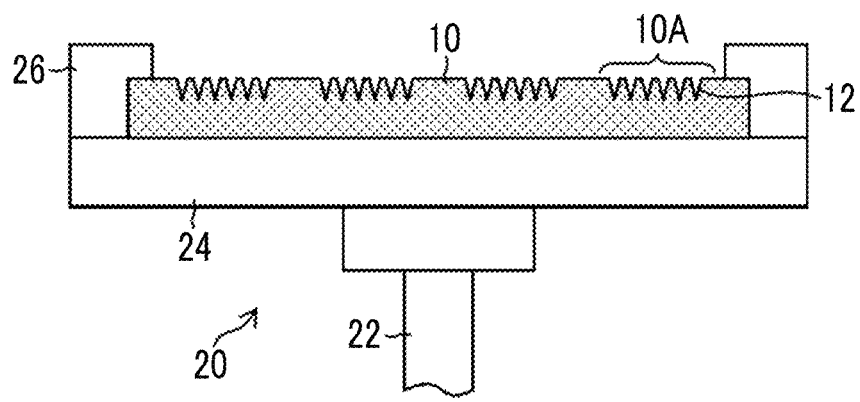
FIG. 1B is a step view showing the procedure of the method of manufacturing an electroforming mold.

Next, FIG. 1B is a view showing a state in which the mold 10 is attached to a cathode 20 used in an electroforming treatment. The cathode 20 includes at least a shaft 22 and a cathode plate 24. The mold 10 is freely detachably attached to the cathode plate 24 by a fixing member 26 at a position where the recessed pattern 10A faces the opposite side of the cathode plate 24. The shaft 22 and the cathode plate 24 are formed of a conductive member. Here, the electroforming treatment refers to a treatment method of precipitating metal on the surface of a mold by an electroplating method.

Figure 1C:
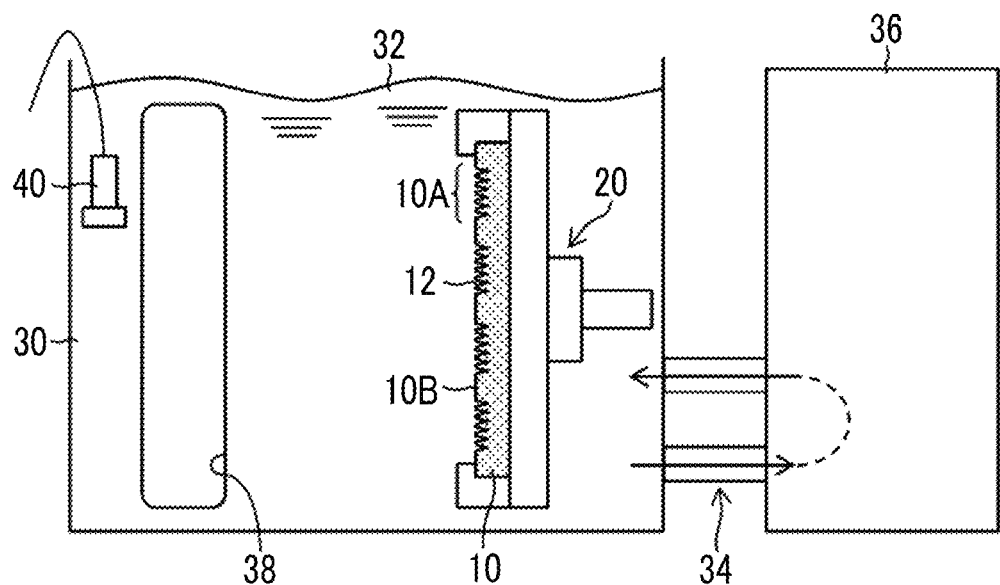
FIG. 1C is a step view showing the procedure of the method of manufacturing the electroforming mold.

Next, FIG. 1C shows a filling step of filling the recessed portions of the recessed patterns 10A of the mold 10 with a degassed pretreatment liquid 32. As shown in FIG. 1C, a pretreatment liquid tank 30 which stores the pretreatment liquid 32 is installed. A vacuum degassing device 36 is connected to the pretreatment liquid tank 30 via a circulation flow passage 34. In addition, an ultrasound oscillator 38 is installed in the pretreatment liquid tank 30. Further, a dissolved oxygen meter 40 is installed in the pretreatment liquid tank 30 to measure the dissolved oxygen concentration of the pretreatment liquid 32. The vacuum degassing device 36 is a device which removes a dissolved gas dissolved in the pretreatment liquid 32 by using a vacuum degassing method.

In the embodiment, in a state in which the mold is attached to the cathode 20, the mold 10 which is a matrix is immersed in the pretreatment liquid 32 stored in the pretreatment liquid tank 30. In a case of immersing the mold 10 in the pretreatment liquid 32, alignment between the surface 10B of the mold 10 on which the recessed patterns 10A are formed and the ultrasound oscillator 38 is performed. The surface 10B of the mold 10 on which the recessed patterns 10A are formed and the ultrasound oscillator 38 are arranged to face each other. Since the ultrasound oscillator 38 and the surface 10B face to each other, ultrasound waves can be effectively applied.

The pretreatment liquid 32 of the pretreatment liquid tank 30 is circulated through the pretreatment liquid tank 30 and the vacuum degassing device 36 by the circulation flow passage 34 and the pretreatment liquid 32 is degassed at the time of passing through the vacuum degassing device 36. The pretreatment liquid degassed therein means a liquid having a dissolved oxygen concentration of 8.0 mg/L or less (at 20° C. and 1 atm (101.325 kPa)). In normal pure water, the dissolved oxygen concentration is about 8.84 mg/L (at 20° C. and 1 atm (101.325 kPa)).

It is preferable that the pretreatment liquid 32 is degassed until the dissolved oxygen concentration of the pretreatment liquid 32 becomes 0.5 mg/L or less. The dissolved oxygen concentration of the pretreatment liquid 32 can be measured by the dissolved oxygen meter 40. For example, in a case of using pure water as the pretreatment liquid 32, by circulating the pretreatment liquid 32 between the pretreatment liquid tank 30 and the vacuum degassing device 36 for about 1 hour, the dissolved oxygen concentration of the pretreatment liquid 32 can be set to 0.5 mg/L or less and thus the degassed pretreatment liquid 32 can be prepared.

By setting the dissolved oxygen concentration of the pretreatment liquid 32 to 0.5 mg/L or less, the gas can be more effectively removed from recessed portions 12 of the mold 10.

The ultrasound waves generated from the ultrasound oscillator 38 are applied to the recessed patterns 10A of the mold 10. The gas present in the recessed portions 12 constituting the recessed patterns 10A is removed by immersing the mold 10 in the degassed pretreatment liquid 32 and applying the ultrasound waves to the recessed patterns 10A, and the recessed portions 12 are filled with the pretreatment liquid 32.

Since the degassed pretreatment liquid 32 is used in the embodiment, there is little gas dissolved in the pretreatment liquid 32. Further, by applying the ultrasound waves to the pretreatment liquid 32, positive and negative pressure is instantaneously applied to the pretreatment liquid 32 and instantaneous generation and disappearance of minute bubbles generated under negative pressure are repeated, so-called cavitation is caused. Thus, the gas in the pretreatment liquid 32 is removed.

Since the ultrasound waves are applied to the needle-like recessed patterns 10A, the gas present in the recessed portions 12 of the recessed patterns 10A can be removed. In addition, since the gas is removed, the recessed portions 12 can be filled with the pretreatment liquid 32. Particularly, the pretreatment liquid 32 can be pushed to the tapered tip end portion of the recessed portion 12 by the ultrasound waves. Here, the ultrasound wave means an ultrasound wave having a frequency of 20 kHz or higher.

As the pretreatment liquid 32 stored in the pretreatment liquid tank 30, pure water, an aqueous solution obtained by dissolving an electroforming liquid component in pure water, or the like can be used.

Figure 2A:
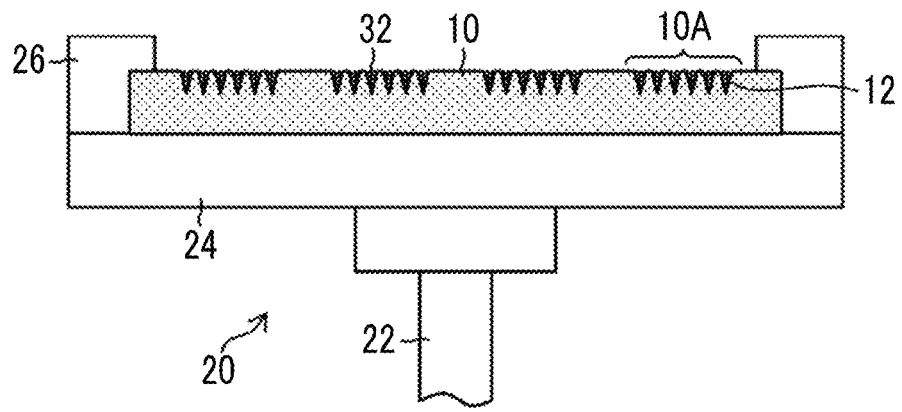
FIG. 2A is a step view showing the procedure of the method of manufacturing the electroforming mold.

FIG. 2A shows a step of taking out the mold 10 which is a matrix from the pretreatment liquid tank 30. As shown in FIG. 2A, in a state in which the mold is attached to the cathode 20, the mold 10 which is a matrix is taken out from the pretreatment liquid tank 30 (not shown). The recessed portions 12 constituting the recessed patterns 10A of the mold 10 are filled with the fully degassed pretreatment liquid 32.

Figure 2B:
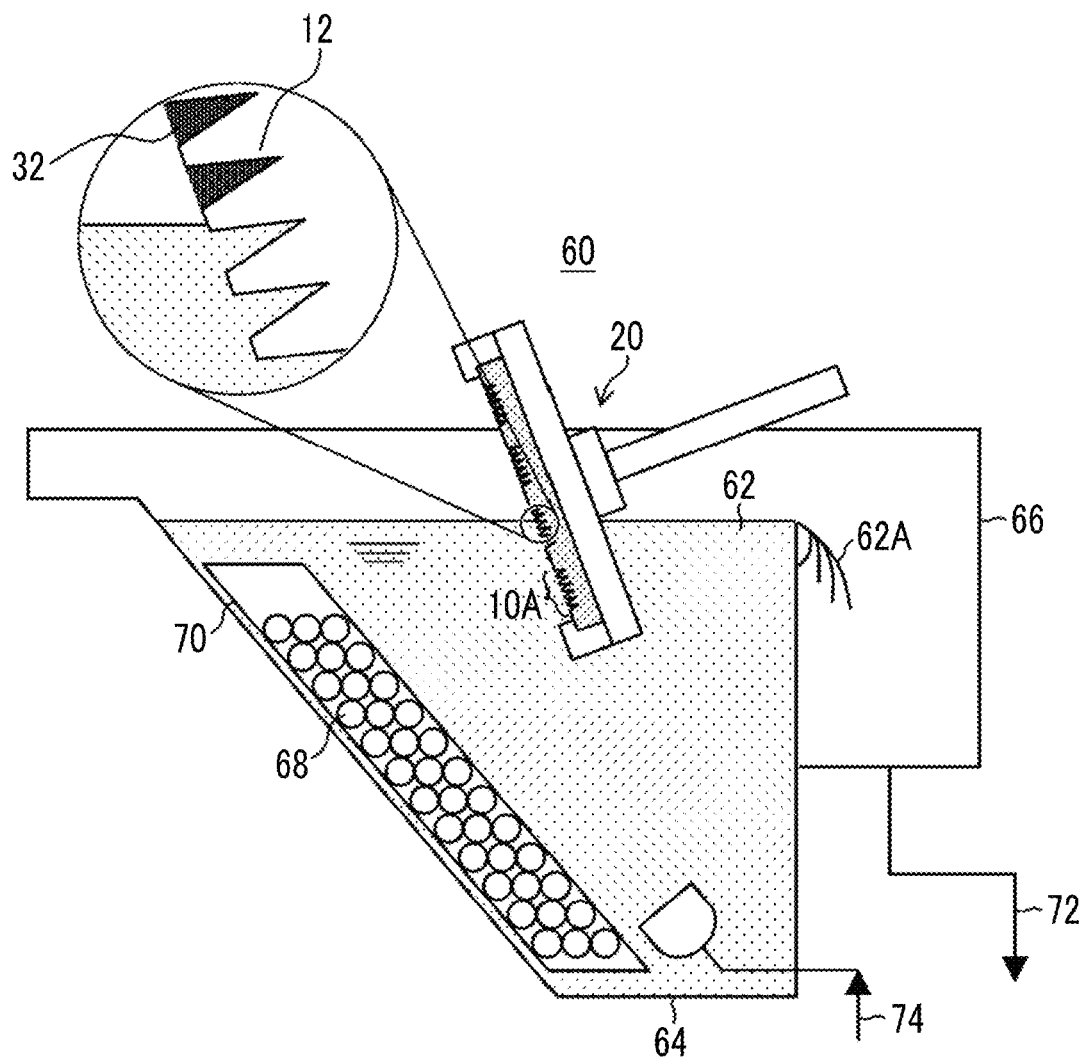
FIG. 2B is a step view showing the procedure of the method of manufacturing the electroforming mold.

FIG. 2B is a view showing a state in a case where the mold 10 which is a matrix and is attached to the cathode 20 is immersed in an electroforming liquid 62. As shown in FIG. 2B, an electroforming device 60, which performs an electroforming treatment on the mold 10, includes an electroforming tank 64 which stores the electroforming liquid 62, a drain tank 66 which receives an electro forming liquid 62A overflowed from the electroforming tank 64, and a titanium case 70 which is filled with Ni pellets 68. The cathode 20 to which the mold 10 is attached is immersed in the electroforming liquid 62 to cause the electroforming device 60 to function.

A drain pipe 72 is connected to the drain tank 66 and a supply pipe 74 is connected to the electroforming tank 64. The electroforming liquid 62 overflowed from the electroforming tank 64 to the drain tank 66 is recovered by the drain pipe 72 and the recovered electroforming liquid 62 is supplied to the electroforming tank 64 from the supply pipe 74.

As described above, before the cathode is immersed in the electroforming liquid 62, the recessed portions 12 of the mold 10 are filled with the degassed pretreatment liquid 32. In the recessed portions 12 of the mold 10, there is no gas. As shown in FIG. 2B, in a case where the mold 10 is immersed in the electroforming liquid 62 in a state in which the recessed portions 12 are filled with the pretreatment liquid 32, the pretreatment liquid 32 filling the recessed portions 12 is replaced with the electroforming liquid 62. By replacing the pretreatment liquid 32 with the electroforming liquid 62, the recessed portions 12 of the mold 10 are filled with the electroforming liquid 62. As a result, intrusion of gas into the recessed portions 12 of the mold 10 is suppressed.

On the other hand, in a case where the recessed portions 12 of the mold 10 are not filled with the pretreatment liquid 32 unlike the present invention, gas is present in the recessed portions 12 of the mold 10. In this state, in a case where the mold 10 is immersed in the electroforming liquid 62, the gas in the recessed portions 12 is not removed and as a result, the recessed portions 12 of the mold 10 are not fully filled with the electroforming liquid 62.

Figure 3A:
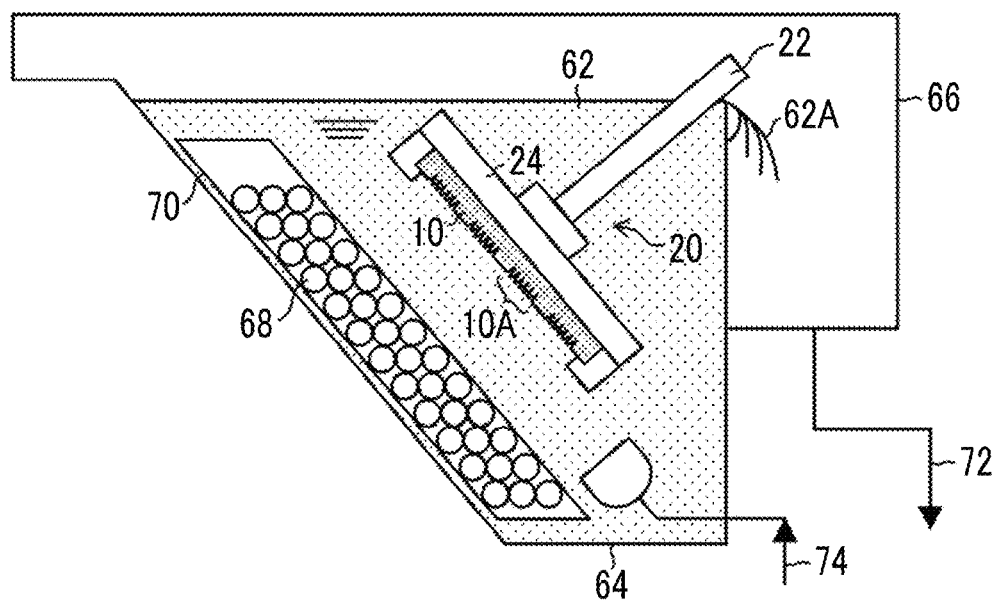
FIG. 3A is a step view showing the procedure of the method of manufacturing the electroforming mold.
Figure 3B:
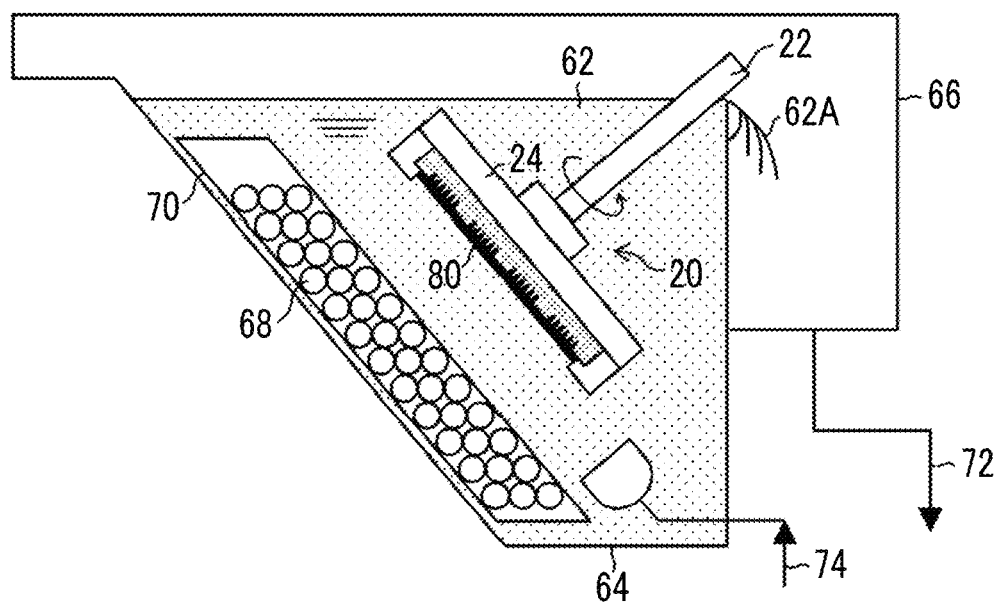
FIG. 3B is a step view showing the procedure of the method of manufacturing the electroforming mold.

FIGS. 3A and 3B show a formation step of immersing the mold 10 which is a matrix in the electroforming liquid 62 stored in the electroforming tank 64 and performing an electroforming treatment to form a metal body 80 on the surface of the mold 10 on which the recessed patterns 10A are formed.

As shown in FIG. 3A, the mold 10 attached to the cathode 20 is completely immersed in the electroforming liquid 62. In a state in which there is no gas in the recessed portions, the recessed portions 12 of the mold 10 are filled with the electroforming liquid 62. In the mold 10 held by the cathode 20, the surface on which the recessed patterns 10A are formed is aligned at a position opposite to the titanium case 70 which becomes an anode.

Next, as shown in FIG. 3B, the cathode 20 is connected to a negative electrode and a positive electrode is connected to the titanium case 70 which becomes an anode. While the mold 10 held on the cathode plate 24 is being rotated about the shaft 22 at a rotation rate of 50 to 150 rpm, a DC voltage is applied between the cathode 20 and the titanium case 70. The Ni pellets 68 are dissolved and the metal body 80 (electroformed film) is formed on the surface of the mold 10 attached to the cathode 20 on which the recessed patterns 10A are formed.

Since the recessed portions 12 are filled with the electroforming liquid 62 in a state in which there is no gas in the recessed portions 12, the metal body 80 can be formed along the shape of the recessed portions 12. Particularly, it is possible to obtain a metal body 80 having no cavity and/or defect in the protruding portions.

As the electroforming liquid 62, for example, a liquid obtained by mixing 400 to 800 g/L of nickel sulfamate, 20 to 50 g/L of boric acid, and required additives such as a surfactant (for example, sodium lauryl sulfate) can be used. The temperature of the electroforming liquid 62 is preferably 40° C. to 60° C.

In a case where the mold 10 is formed of a resin material, first, a conduction treatment is preferably performed on the mold 10. For example, a metal (for example, nickel) is sputtered on the mold 10 to cause the metal to adhere to the surface of the mold 10 and the recessed patterns 10A.

Figure 4A:
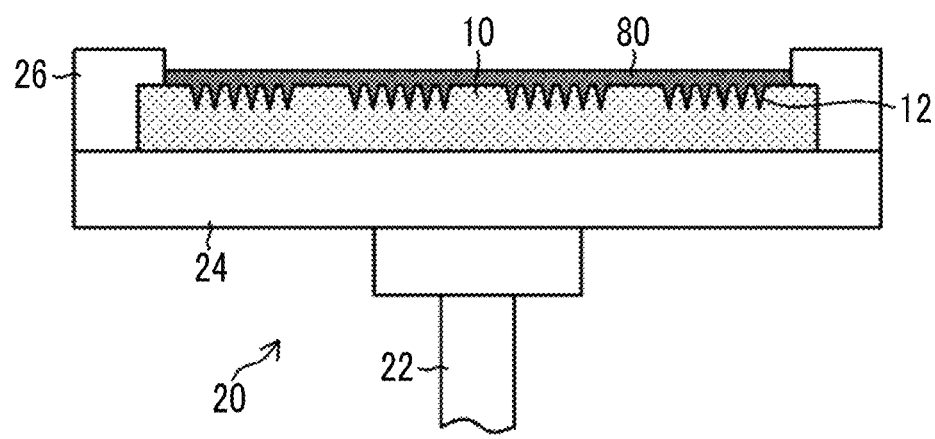
FIG. 4A is a step view showing the procedure of the method of manufacturing the electroforming mold.
Figure 5:
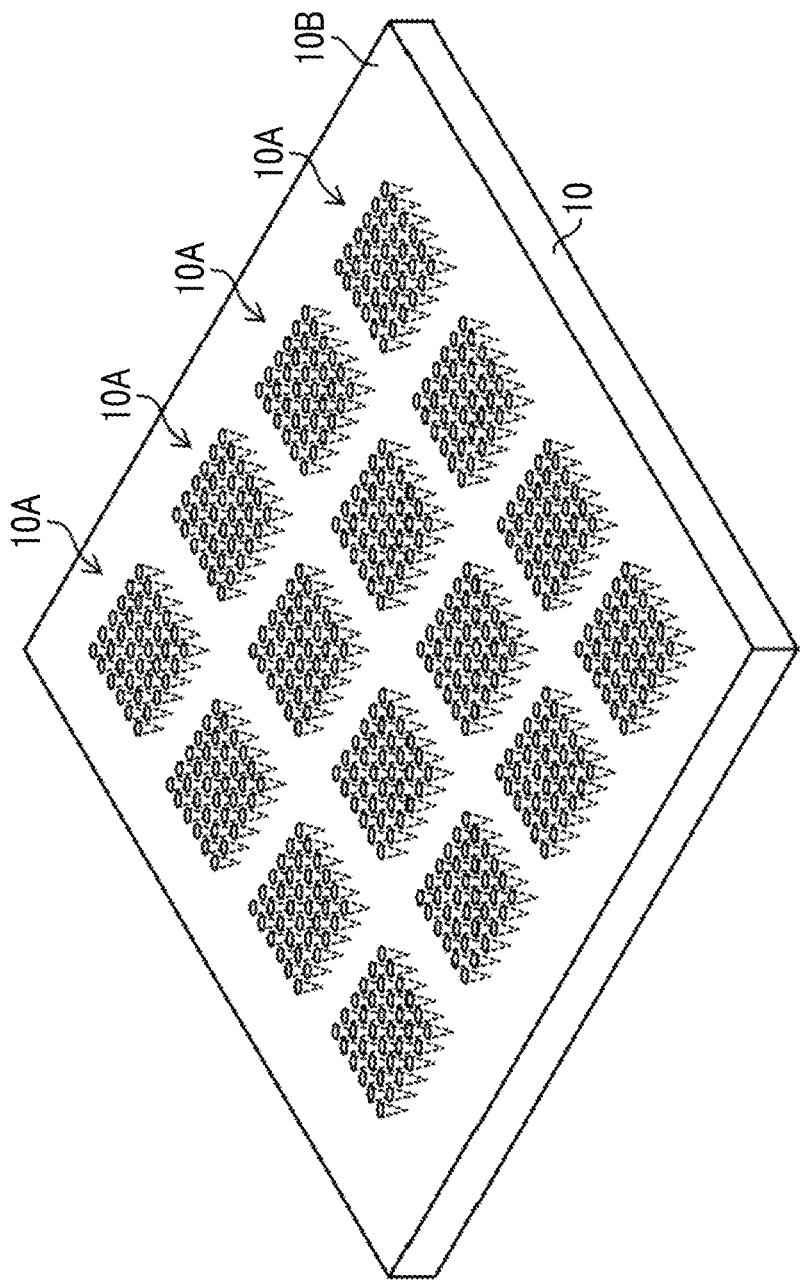
FIG. 5 is a perspective view showing a mold which is a matrix.

As shown in FIG. 4A, in a case where the metal body 80 is formed on the surface of the mold 10 on which the recessed patterns are formed, the cathode 20 to which the mold 10 is attached is taken out from the electroforming tank 64 (not shown).

Figure 4B:
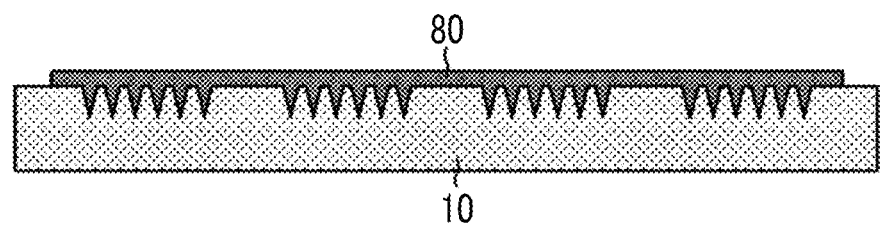
FIG. 4B is a step view showing the procedure of the method of manufacturing the electroforming mold.

Next, as shown in FIG. 4B, the mold 10 on which metal body 80 is formed is detached from the cathode 20.

Figure 4C:
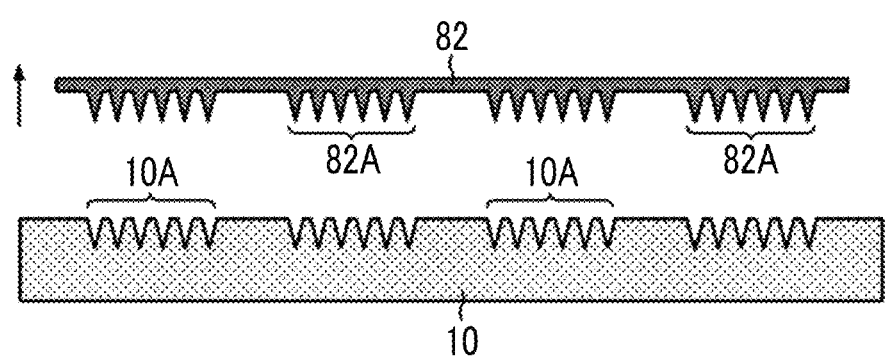
FIG. 4C is a step view showing the procedure of the method of manufacturing the electroforming mold.

FIG. 4C shows a peeling-off step for obtaining an electroforming mold 82. As shown in FIG. 4C, the metal body 80 is peeled off from the mold 10 which is a matrix to obtain an electroforming mold 82 having protruding patterns 82A. The protruding pattern 82A has an inverted shape of the recessed pattern 10A of the mold 10. The electroforming mold 82 is the metal body 80 peeled off from the mold 10.

Since the metal body 80 having no cavity and/or defect in the protruding portions can be obtained as described above, as a result, the electroforming mold 82 having the protruding patterns 82A with no cavity and/or defect can be obtained.

Next, the method of manufacturing the mold 10 having the recessed patterns 10A, which is a matrix, will be described with reference to FIGS. 6A to 7C. FIGS. 6A to 7C show step views showing the procedure of the method of manufacturing the mold 10 which is a matrix. It is preferable that the mold 10 which is a matrix is formed of a resin material. This is because the mold 10 is easily manufactured.

Figure 6A:
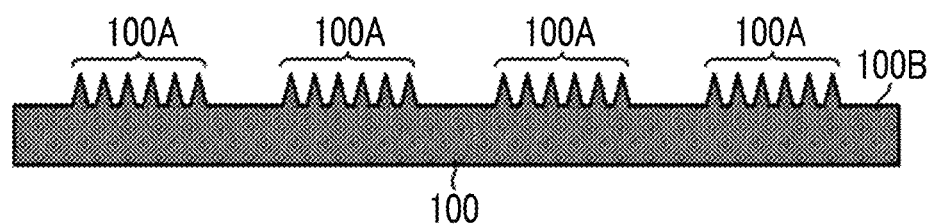
FIG. 6A is a step view showing a procedure of a method of manufacturing a matrix.

The procedure of the method of manufacturing the mold 10, which is a matrix, shown in FIGS. 6A to 6C will be described. FIG. 6A shows a state in which an original plate 100 is prepared. An original plate 100 having protruding patterns 100A is manufactured by, for example, machining a metal substrate, which becomes the original plate 100, by using a cutting tool such as a diamond bite. As the metal substrate, substrates of stainless steel, an aluminum alloy, Ni, and the like can be used. In the embodiment, the original plate 100 having a plurality of protruding patterns 100A is manufactured.

The protruding pattern 100A refers to a state in which protruding portions protruding in a direction away from a flat surface 100B of the original plate 100 are arranged on the flat surface 100B of the original plate 100. The number of protruding portions, the arrangement positions of the protruding portions, and the like are not limited.

The protruding portion constituting the protruding pattern 100A may be constituted of a tapered needle portion in a direction away from the flat surface 100B, may be constituted of a frustum portion and a tapered needle portion in a direction away from the flat surface 100B, or may be constituted of a frustum portion, a columnar portion, and a tapered needle portion in a direction away from the flat surface 100B.

For example, the protruding portion preferably has a height of 100 to 2000 μm from the flat surface 100B of the original plate 100 and a tip end diameter Φ of 50 μm or less. In a case where a plurality of protruding portions are provided, an interval between adjacent protruding portions is preferably 300 to 2000 μm. The aspect ratio of the protruding portion (the height of the protruding portion/the width of the bottom surface of the protruding portion) is preferably 1.2 to 8.0.

Figure 6B:
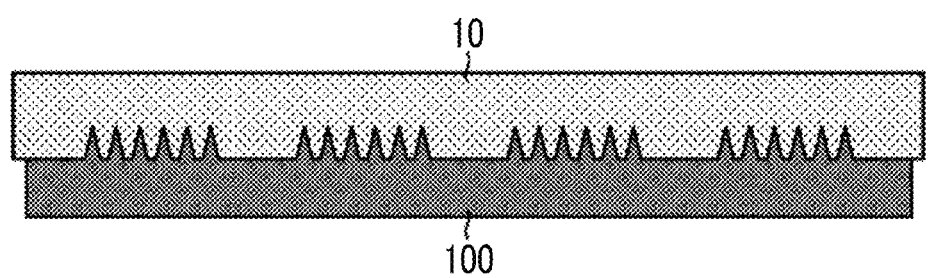
FIG. 6B is a step view showing the procedure of the method of manufacturing the matrix.
Figure 6C:
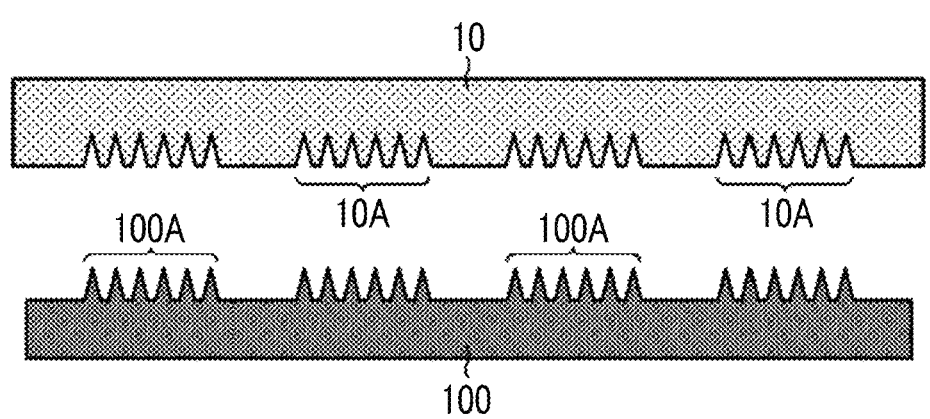
FIG. 6C is a step view showing the procedure of the method of manufacturing the matrix.

FIGS. 6B and 6C are step views showing steps of manufacturing the resin mold 10 having the recessed patterns 10A using the original plate 100 having the protruding patterns 100A. The recessed pattern 10A refers to a state in which recessed portions extending from one surface of the mold 10 to the other surface thereof are arranged on one surface of the mold 10. The number of recessed portions, the arrangement position of the recessed portions, and the like are not limited.

The mold 10 having the recessed patterns 10A, which becomes a matrix, can be manufactured by first to third methods described below.

First, the first method will be described. An ultraviolet curable resin that is cured by irradiation with ultraviolet rays is prepared. The protruding patterns 100A of the original plate 100 are pressed against the ultraviolet curable resin. In a state in which the original plate 100 is pressed against the ultraviolet curable resin, the ultraviolet curable resin is irradiated with ultraviolet rays to cure the ultraviolet curable resin. The original plate 100 is released from the cured ultraviolet curable resin. The resin mold 10 having the recessed patterns 10A having an inverted shape of the protruding pattern 100A of the original plate 100 is manufactured.

The ultraviolet curable resin refers to a resin that is cured by irradiation with ultraviolet rays through a crosslinking reaction and a polymerization reaction. Examples of ultraviolet polymerizable functional groups include unsaturated polymerizable functional groups such as a (meth)acryloyl group, a vinyl group, a styryl group, and an allyl group.

The second method will be described. A thermoplastic resin which is the material for the mold 10 is prepared. The original plate 100 having the protruding patterns 100A is heated. The protruding patterns 100A of the heated original plate 100 are pressed against the surface of the thermoplastic resin. Since the surface of the thermoplastic resin is softened, the surface of the thermoplastic resin is deformed along the shape of the protruding pattern 100A.

In a state in which the original plate 100 is pressed against the thermoplastic resin, the original plate 100 is cooled. The thermoplastic resin is cured by cooling the original plate 100. Thereafter, the original plate 100 is released from the thermoplastic resin to which the protruding pattern 100A are transferred. The resin mold 10 having the recessed patterns 10A having an inverted shape of the protruding pattern 100A of the original plate 100 is manufactured.

As the material for a thermoplastic resin 14, low density polyethylene (LDPE), high density polyethylene (HDPE), polypropylene (PP), polycarbonate (PC), and the like can be used.

Next, the third method will be described. A silicone resin obtained by adding a curing agent to polydimethylsiloxane (PDMS, for example, SILGUARD 184 manufactured by Dow Corning Co. Ltd., SYLGARD: registered trademark) is prepared. The protruding patterns 100A of the original plate 100 are pressed against the silicone resin. In a state in which the original plate 100 is pressed against the silicone resin, the silicone resin is cured by a heat treatment at 100° C. The original plate 100 is released from the cured silicone resin. The mold 10 which has the recessed patterns 10A having an inverted shape of the protruding pattern 100A of the original plate 100 and becomes a resin matrix is manufactured. The method of manufacturing the mold 10 is not limited to the first to third methods.

Figure 7A:
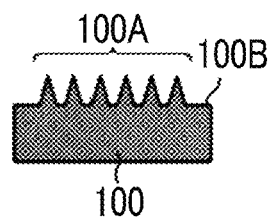
FIG. 7A is a step view showing a procedure of a method of manufacturing another matrix.

Next, the procedure of the method of manufacturing the mold 10 which is a matrix shown in FIGS. 7A to 7C will be described. FIG. 7A shows a state in which an original plate 100 is prepared. An original plate 100 having a protruding pattern 100A is manufactured by, for example, machining a metal substrate which becomes the original plate 100 by using a cutting tool such as a diamond bite. As the metal substrate, substrates of stainless steel, an aluminum alloy, Ni, and the like can be used. In the embodiment, the original plate 100 having one protruding pattern 100A is manufactured.

The meaning of the protruding pattern 100A, the shape of the protruding portion, the size thereof, and the like are the same as in FIGS. 6A to 6C.

Figure 7B:
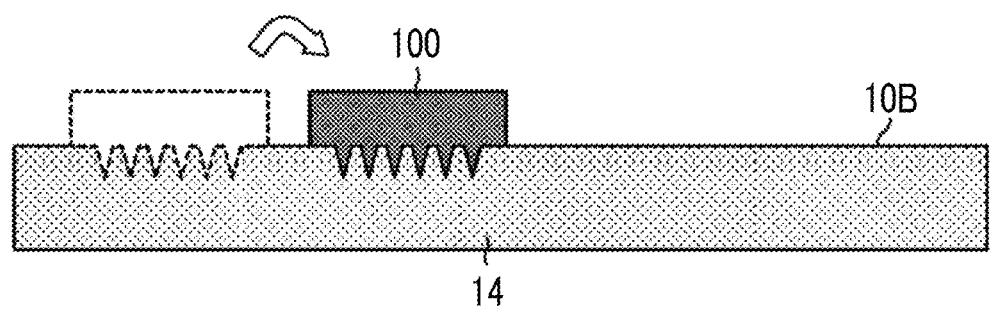
FIG. 7B is a step view showing the procedure of the method of manufacturing the other matrix.
Figure 7C:
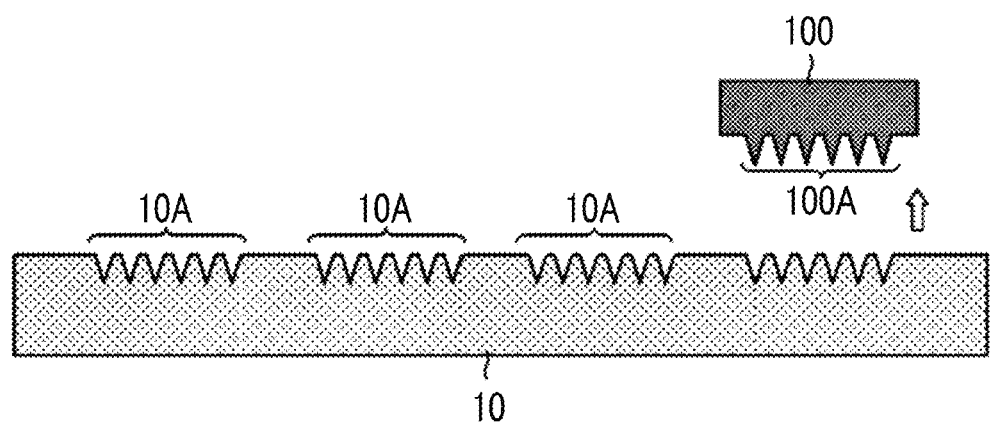
FIG. 7C is a step view showing the procedure of the method of manufacturing the other matrix.

FIGS. 7B and 7C are step views showing steps of manufacturing the resin mold 10 having the recessed patterns 10A using the original plate 100 having the protruding pattern 100A.

As shown in FIG. 7B, the sheet-like thermoplastic resin 14 which becomes the mold 10 is prepared. The original plate 100 and the sheet-like thermoplastic resin 14 are moved relative to each other to determine the position where the original plate 100 is pressed against the thermoplastic resin 14.

The original plate 100 is heated to the softening temperature of the thermoplastic resin 14 or higher. The original plate 100 is pressed against the surface 10B side of the thermoplastic resin 14. The protruding pattern 100A of the original plate 100 is pressed against the thermoplastic resin 14. Next, by cooling the original plate 100 in a state in which the original plate 100 is pressed against the thermoplastic resin 14, the thermoplastic resin 14 is cooled until the temperature is reduced to the softening temperature or lower.

The original plate 100 and the thermoplastic resin 14 are separated by pulling to form a recessed pattern 10A having an inverted shape of the protruding pattern 100A on the surface 10B side of the thermoplastic resin 14.

After the formation of the recessed pattern 10A is completed, in another region of the thermoplastic resin 14, the position of the original plate 100 and the thermoplastic resin 14 is determined. Next, the heated original plate 100 is pressed against the surface 10B side of the thermoplastic resin 14. By cooling the original plate 100 in a state in which the original plate 100 is pressed against the thermoplastic resin 14, the thermoplastic resin 14 is cooled until the temperature is reduced to the softening temperature or lower.

The position determination of the original plate 100 and the thermoplastic resin 14 and the formation of the recessed pattern 10A on the surface 10B side of the thermoplastic resin 14 are repeated by a required number of times.

The formation of the recessed pattern 10A on the thermoplastic resin 14 is completed and thus the mold 10, which becomes a matrix, is manufactured.

Figure 8A:
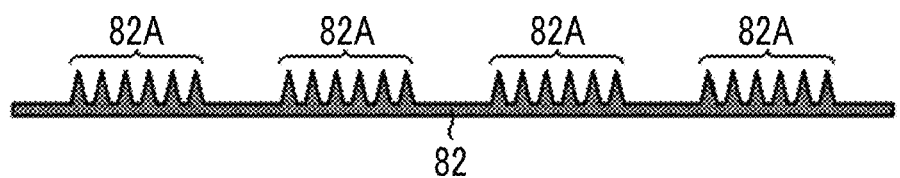
FIG. 8A is a step view showing a procedure of a method of manufacturing a mold using an electroforming mold.
Figure 8B:
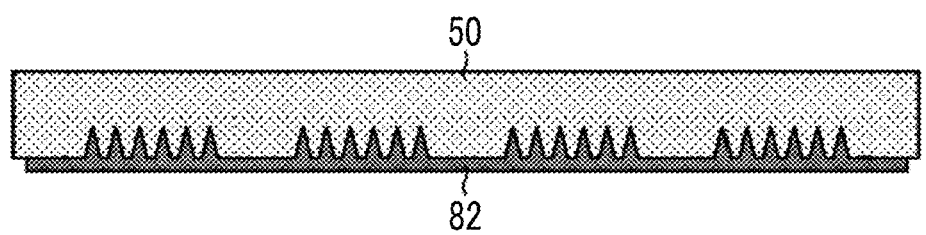
FIG. 8B is a step view showing the procedure of the method of manufacturing the mold using the electroforming mold.
Figure 8C:
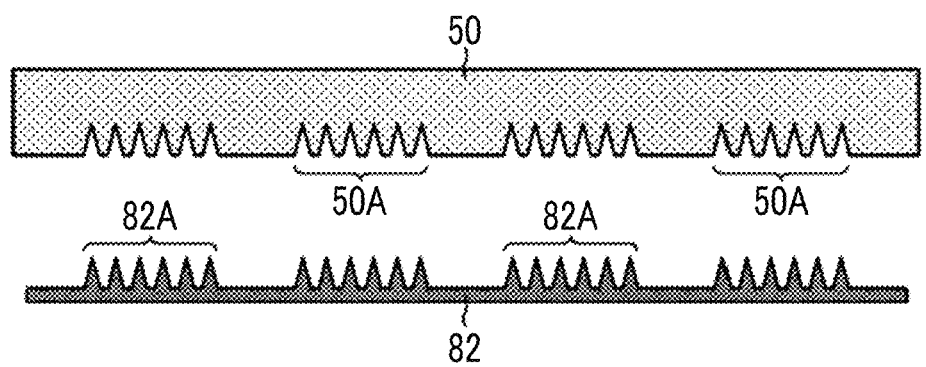
FIG. 8C is a step view showing the procedure of the method of manufacturing the mold using the electroforming mold.

Next, a method of manufactured a mold using the electroforming mold 82 will be described. FIGS. 8A to 8C are step views showing a procedure of a method of manufacturing a mold 50 using the electroforming mold 82.

FIG. 8A shows a state in which the electroforming mold 82 is prepared. The electroforming mold 82 is manufactured by the above-described method of manufacturing an electroforming mold. The electroforming mold 82 includes protruding patterns 82A on one surface.

FIGS. 8B and 8C are step views showing steps of manufacturing a resin mold 50 having recessed patterns 50A having an inverted shape of the protruding pattern 82A of the electroforming mold 82 using the electroforming mold 82 having the protruding patterns 82A. The recessed pattern 50A refers to a state in which recessed portions extending from one surface of the mold 50 to the other surface are arranged on one surface of the mold 50. The number of recessed portions, the arrangement position of the recessed portions, and the like are not limited.

The method of manufacturing the mold 50 using the electroforming mold 82 will be described. By the following first to third methods, the mold 50 having the recessed patterns 50A can be manufactured. Basically, the method of manufacturing the mold 10 as a matrix from the original plate 100 shown in FIGS. 6A to 6C can be suitably used.

First, the first method will be described. An ultraviolet curable resin that is cured by irradiation with ultraviolet rays is prepared. The protruding patterns 82A of the electroforming mold 82 are pressed against the ultraviolet curable resin. In a state in which the electroforming mold 82 is pressed against the ultraviolet curable resin, the ultraviolet curable resin is irradiated with ultraviolet rays to cure the ultraviolet curable resin. The electroforming mold 82 is peeled off from the cured ultraviolet curable resin. The resin mold 50 with the recessed patterns 50A having an inverted shape of the protruding pattern 82A of the electroforming mold 82 can be manufactured.

The second method will be described. A sheet-like thermoplastic resin which is the material for the mold 50 is prepared. The electroforming mold 82 having the protruding patterns 82A is heated. The protruding patterns 82A of the heated electroforming mold 82 are pressed against the surface of the thermoplastic resin. Since the surface of the thermoplastic resin is softened, the protruding patterns 82A are transferred to the thermoplastic resin.

In a state in which the electroforming mold 82 is pressed against the thermoplastic resin, the electroforming mold 82 and the thermoplastic resin are cooled. The thermoplastic resin is cured by cooling the electroforming mold 82. Thereafter, the electroforming mold 82 is peeled off from the thermoplastic resin to which the protruding patterns 82A are transferred. The resin mold 50 having the recessed patterns 50A having an inverted shape of the protruding pattern 82A of the electroforming mold 82 can be manufactured.

Next, the third method will be described. A silicone resin obtained by adding a curing agent to polydimethylsiloxane (PDMS, for example, SILGUARD 184 manufactured by Dow Coming Co. Ltd.) is prepared. The protruding patterns 82A of the electroforming mold 82 are pressed against the silicone resin. In a state in which the electroforming mold 82 is pressed against the silicone resin, the silicone resin is cured by a heat treatment at 100° C. The electroforming mold 82 is peeled off from the cured silicone resin. The resin mold 50 which has the recessed patterns 50A having an inverted shape of the protruding pattern 82A of the electroforming mold 82 can be manufactured.

Since the recessed pattern 50A has an inverted shape of the protruding pattern 82A, the size of each recessed portion of the recessed pattern 50A is almost the same as the size of each protruding portion of the protruding pattern 82A. However, the method of manufacturing the mold 50 is not limited to the first to third methods.

Next, a method of producing a transdermal absorption sheet having a protruding pattern, which is a molded article having a fine pattern, using the mold 50 will be described. FIGS. 9A to 9G are step views showing a procedure of a method of producing a transdermal absorption sheet using the mold 50.

Figure 9A:
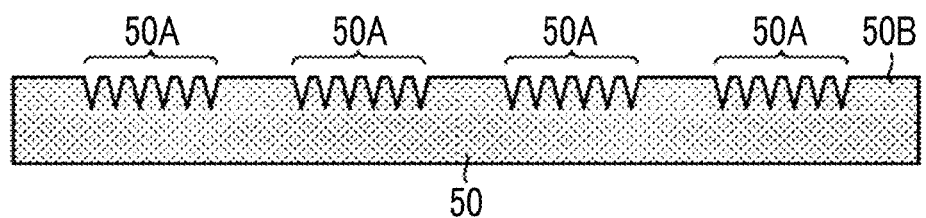
FIG. 9A is a step view showing a procedure of a method of producing a transdermal absorption sheet.

FIG. 9A shows a state in which the mold 50 is prepared. The mold 50 is manufactured by the method of manufactured a mold shown in FIGS. 8A to 8C. On a surface 50B of the mold 50, the recessed patterns 50A are formed.

Figure 9B:
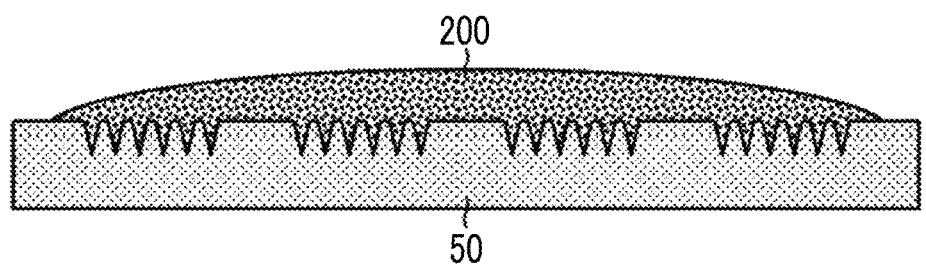
FIG. 9B is a step view showing the procedure of the method of producing the transdermal absorption sheet.

FIG. 9B shows a supply step of supplying a polymer solution to the recessed patterns 50A of the mold 50.

First, a polymer solution 200 is prepared. As the material for a resin polymer used in the polymer solution 200, a resin having biocompatibility is preferably used. As such a resin, it is preferable to use saccharides such as glucose, maltose, pullulan, sodium chondroitin sulfate, sodium hyaluronate, hydroxyethyl starch or hydroxypropyl cellulose, proteins such as gelatin, or a biodegradable polymer such as polylactic acid or a lactic acid/glycolic acid copolymer. Among these, a gelatin-based material has adhesiveness with many base materials and has a high gel strength as a material to be gelated. Thus, the gelatin-based material can be preferably used in a peeling-off step to be described below since the gelatin-based material can be brought into close contact to the base material to allow the polymer sheet to be peeled off from the mold 50 using the base material.

As the material for forming a transdermal absorption sheet 220, it is preferable to use a water-soluble material. The use of a water-soluble material as the material for the transdermal absorption sheet 220 facilitates dissolution of a protruding pattern in a case where a protruding pattern 220A formed on the transdermal absorption sheet 220 is inserted into the skin and allows easy injection of a chemical. Accordingly, it is preferable that the polymer solution 200 includes a water-soluble material. Here, the water-soluble material means a material that is soluble in water.

A drug can be contained in the polymer solution 200. The drug contained in the polymer solution 200 is not particularly limited as long as the drug is a material having bioactivity. The drug is preferably selected from a peptide, a protein, a nucleic acid, a polysaccharide, a vaccine, a pharmaceutical compound, and a cosmetic component. The pharmaceutical compound preferably belongs to a water-soluble low molecular weight compound. Here, the low molecular weight compound means a compound having a molecular weight of several hundreds to several thousands.

It is preferable that the concentration of the resin is set such that 10 to 50% by mass of resin polymer is contained in the polymer solution 200 not containing a drug, although the concentration varies depending on the material. In addition, a solvent used for dissolution may be other than hot water as long as the solvent has volatility, and methylethylketone, alcohol, or the like can be used. Then, a drug to be supplied to the inside of a human body may concurrently be dissolved into a solution of the polymer resin in accordance with the application. It is preferable that the polymer concentration (the concentration of a polymer excluding a drug in a case where the drug itself is a polymer) of the polymer solution 200 containing a drug is in a range of 0% to 40% by mass.

In the method of preparing the polymer solution 200, in a case of using a water-soluble polymer (gelatin or the like), a water-soluble powder may be dissolved into water and after the dissolution, a drug may be added to the solution. Alternatively, a water-soluble polymer powder may be poured and dissolved in a liquid containing a drug dissolved therein. In a case where the polymer is difficult to dissolve into water, the polymer may be dissolved on heating. The temperature may be selected, as appropriate, depending on the kind of the polymer material, but the solution is preferably heated to a temperature of about 60° C. or lower. The viscosity of the solution of the polymer resin is preferably 100 Pa·s or less, and more preferably 10 Pa·s or less for the solution containing a drug. The viscosity of the solution of the polymer resin is preferably 2,000 Pa·s or less, and more preferably 1,000 Pa·s or less for the solution not containing a drug. Appropriate adjustment of the viscosity of the solution of the polymer resin facilitates injection of the solution into the needle-like recessed portions of the mold. For example, the viscosity of the solution of the polymer resin can be measured with a capillary viscometer, a falling ball type viscometer, a rotary viscometer, or a vibration type viscometer.

As shown in FIG. 9B, the polymer solution 200 is supplied to the mold 50 to fill the recessed patterns 50A with the polymer solution 200. That is, the recessed portions constituting the recessed patterns 50A are filled with the polymer solution 200.

As the method of filling the recessed patterns 50A with the polymer solution 200, a method of performing filling using a spin coater, a method of performing filling by moving a squeegee, a method of performing filling while moving a slit nozzle, a method of performing filling of the recessed portions of the recessed patterns 50A using a dispenser, or the like can be employed.

As disclosed in WO2014/077242, it is preferable that in a state in which the slit nozzle is brought into contact with the surface of the mold 50, the polymer solution 200 is supplied to the recessed patterns 50A while moving the slit nozzle and the mold relative to each other. In the case where the slit nozzle and the mold 50 are moved relative to each other in the state in which the slit nozzle is brought into contact with the surface of the mold 50, the surface of the mold 50 preferably has flatness.

A case where it is difficult for the polymer solution 200 to reach the corner of each recessed portion of the recessed pattern 50A of the mold 50 due to the presence of the air is considered. Accordingly, the supply step is desirably performed under an environment at reduced pressure. The environment at reduced pressure means a state at or below atmospheric pressure. For example, by setting the mold 50 in a depressurization device (not shown) and supplying the polymer solution 200 to the mold 50, the polymer solution 200 can be supplied to the tip ends of the recessed patterns 50A while the air is released from the recessed portion under the environment at reduced pressure. It is particularly effective to perform the supply step under the environment at reduced pressure in a case where the mold 50 is a gas permeable material.

As another method, the mold 50 supplied with the polymer solution 200 is placed in a pressure resistant vessel.

After heating the inside of the pressure resistant vessel to 40° C. using a heating jacket, compressed air is injected into the pressure resistant vessel from a compressor. The air in the recessed portion is removed by holding the inside of the pressure resistant vessel at a pressure of 0.5 MPa for 5 minutes and applying pressure thereto, thereby enabling the polymer solution 200 to be supplied to the tip ends of the recessed patterns 50A of the mold 50.

Figure 9C:
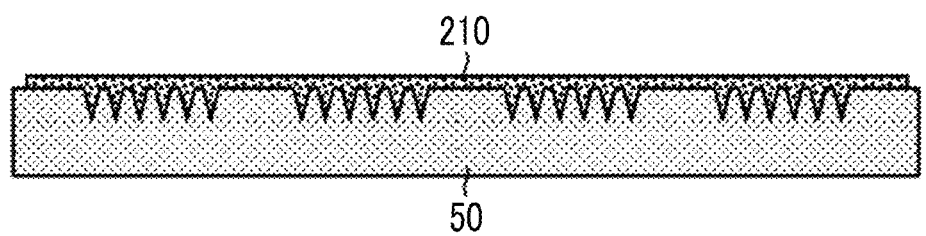
FIG. 9C is a step view showing the procedure of the method of producing the transdermal absorption sheet.

FIG. 9C shows a drying step of drying the polymer solution 200 to form a polymer sheet 210. For example, the polymer solution 200 supplied to the mold 50 can be dried by blowing air thereto.

Drying is divided into, for example, four zones, and by setting conditions including (1) set dry at 15° C. (low humidity, wind speed 4 m/sec), (2) light wind drying at 35° C. (low humidity, wind speed 8 m/sec), (3) strong wind drying at 50° C. (wind speed 12 m/sec), and (4) strong wind drying at 30° C. (wind speed 20 m/sec), efficient drying can be performed.

By drying the applied polymer solution 200 or drying the polymer solution after gelating the polymer solution 200, the polymer solution is solidified to form the polymer sheet 210. By gelating the polymer solution 200, the shape thereof can be reduced and peelability from the mold 50 can be enhanced. In this case, the polymer solution 200 can be gelated by flowing cold air at a low humidity. In order to completely gelate the polymer solution, cold air at 10° C. to 15° C. is blown for a longer period of time than in the above case, and thereafter air is blown in the same manner as above. In addition, in this case, during flowing of hot air at a high temperature for subsequent drying, in a case where the temperature of hot air is too high, gelation of the polymer solution 200 is cancelled or the effect of the drug may change due to decomposition of the drug through heating. Therefore, the temperature of the blown air requires attention.

By forming the polymer sheet 210, the polymer sheet is reduced in size compared to the state at the injection of the polymer solution 200. Particularly, in a case where gelation is performed, the polymer sheet is significantly reduced in size. Accordingly, peeling of the polymer sheet 210 from the mold 50 which will be described later is facilitated.

The polymer sheet 210 means a state after a desired drying treatment is applied to the polymer solution 200. The moisture content of the polymer sheet 210 and the like are appropriately set.

Figure 9D:
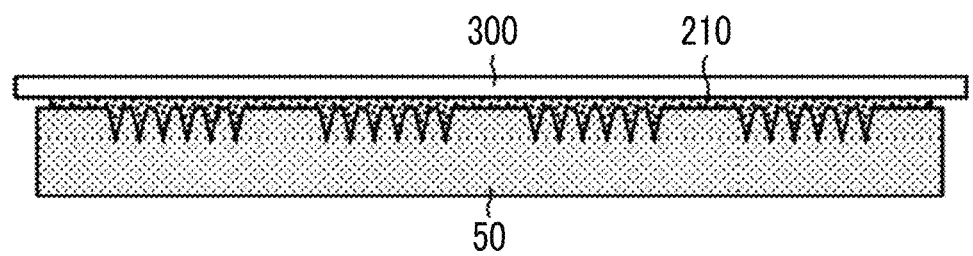
FIG. 9D is a step view showing the procedure of the method of producing the transdermal absorption sheet.
Figure 9E:
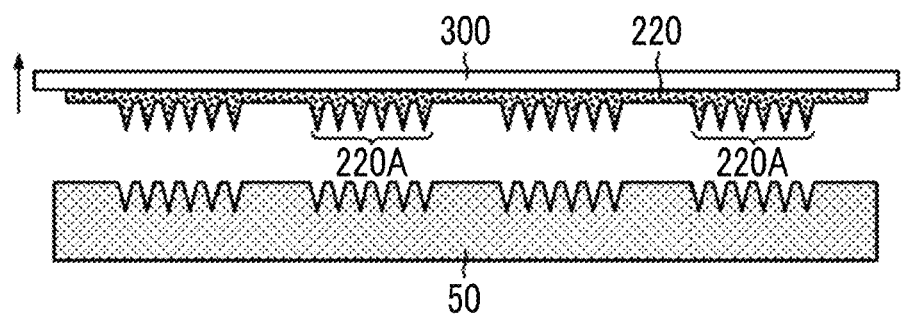
FIG. 9E is a step view showing the procedure of the method of producing the transdermal absorption sheet.

FIGS. 9D and 9E show a polymer sheet peeling-off step of peeling off the polymer sheet 210 from the mold 50. As shown in FIG. 9D, a sheet-like base material 300 having a pressure sensitive adhesive layer formed thereon is attached to the surface of the polymer sheet 210 opposite to the mold 50. The surface of the base material 300 may be subjected to a surface activation treatment so as to be bonded. Furthermore, after the base material 300 is brought into close contact to the polymer sheet, the polymer solution may be applied thereto from above the base material 300 to bury the base material 300 therein. As the material for the sheet-like base material 300, for example, polyethylene terephthalate (PET), polypropylene (PP), polycarbonate (PC), polyethylene (PE), or the like can be used.

As shown in FIG. 9E, after the base material 300 is attached to the polymer sheet 210, the base material 300 and the polymer sheet 210 are simultaneously peeled off. A sucker (not shown) is installed on the surface of the base material 300 opposite to the bonding surface of the polymer sheet 210 and is pulled up vertically while sucking the base material 300 with air. The polymer sheet 210 is peeled off from the mold 50, thereby forming a transdermal absorption sheet 220 having protruding patterns 220A.

It is preferable that the material forming the mold 50 is formed of a material which is very easily peelable. In addition, by using a highly elastic and soft material as the material forming the mold 50, stress applied to the protruding patterns 220A of the transdermal absorption sheet 220 during peeling-off can be relieved.

The protruding pattern 220A of the transdermal absorption sheet 220 has an inverted shape of the recessed pattern 50A of the mold 50. Here, the transdermal absorption sheet 220 is basically the same as the polymer sheet 210 peeled off from the mold 50.

Figure 9F:
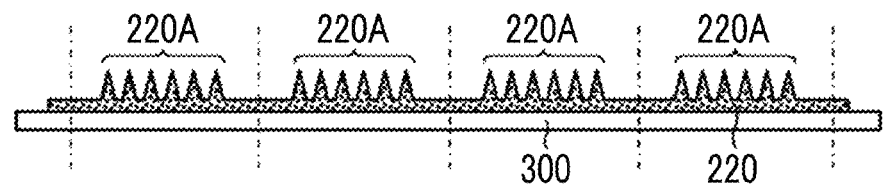
FIG. 9F is a step view showing the procedure of the method of producing the transdermal absorption sheet.
Figure 9G:
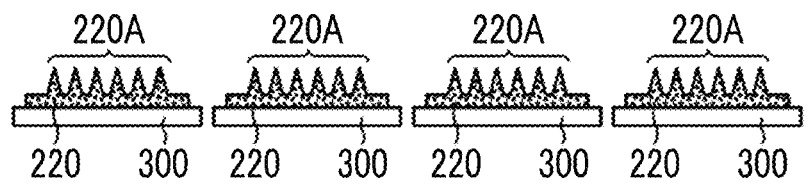
FIG. 9G is a step view showing the procedure of the method of producing the transdermal absorption sheet.

FIGS. 9F and 9G show a cutting step of cutting the transdermal absorption sheet 220 into individual transdermal absorption sheets 220.

As shown in FIG. 9F, the transdermal absorption sheet 220 having the protruding pattern 220A and the base material 300 peeled from the mold 50 are set in a cutting device (not shown). The positions to cut the transdermal absorption sheet 220 are determined. Basically, the cutting position is determined for each protruding pattern 220A.

As shown in FIG. 9G, the transdermal absorption sheet 220 is cut into a plurality of individual transdermal absorption sheets 220. In the embodiment, an example in which the transdermal absorption sheet 220 and the base material 300 are simultaneously cut is described, but the present invention is not limited thereto.

For example, the base material 300 may be peeled off from the transdermal absorption sheet 220 and the base material 300 peeled off from the mold 50, and the transdermal absorption sheet 220 may be cut into the individual transdermal absorption sheets 220.

In this embodiment, the case where the polymer sheet 210 is formed by filling the recessed patterns 50A with the polymer solution 200 and drying the polymer solution 200 is described, but the present invention is not limited thereto.

For example, a polymer sheet can be formed by filling the recessed patterns 50A with the polymer solution 200 containing a drug, drying the polymer solution 200, filling the recessed patterns 50A with the polymer solution 200 which does not contain a drug, and drying the polymer solution 200.

As long as the polymer solution 200 capable of forming the transdermal absorption sheet 220 is supplied, the number of times the polymer solution 200 is supplied and the presence or absence of the drug in the polymer solution 200 can be appropriately changed.

Figure 10:
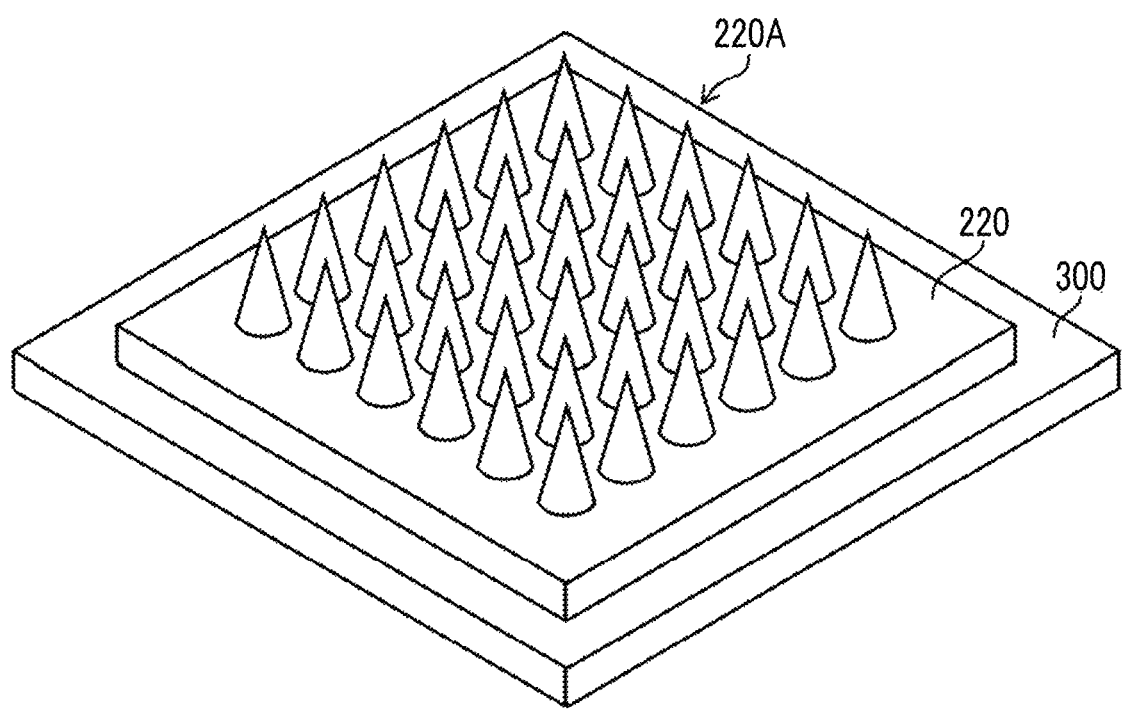
FIG. 10 is a perspective view of an individual transdermal absorption sheet.

FIG. 10 is a perspective view showing the individual transdermal absorption sheet 220. The individual transdermal absorption sheet 220 has the protruding pattern 220A on one surface. In addition, the transdermal absorption sheet 220 has the base material 300 on the surface opposite to the surface on which the protruding pattern 220A is formed.

According to the embodiment, bubbles can be removed from the mold attached to the cathode and an electroforming mold having no cavity and/or defect can be manufactured. A mold can be manufactured using the manufactured electroforming mold. A transdermal absorption sheet can be produced using the manufactured mold.

EXAMPLES

Hereinafter, the present invention will be described in more detail using examples of the present invention. The materials, used amounts, ratios, treatment contents, treatment procedures, and the like shown in the following examples can be appropriately changed without departing from the gist of the present invention. Therefore, the scope of the present invention should not be interpreted in a limited manner based on the specific examples illustrated below.

(Basic Conditions)

Approximately conical recessed portions having a bottom surface diameter of 0.6 mm were formed on the surface of a linear low density polyethylene (LLDPE) material having a thickness of 1.5 mm in a size φ of 8 inches at a depth of 0.9 mm with a pitch of 1 mm. Thus, a LDPE matrix having needle-like recessed patterns was prepared. A Ni film having a thickness of 0.2 μm was formed on the matrix having the recessed patterns by a sputtering treatment as a pretreatment for the matrix. The pretreated matrix was immersed in an electroforming liquid stored in an electroforming tank and temperature-controlled at 45° C., and after the matrix was immersed, an electroforming treatment was performed such that an electroforming mold having a thickness of 0.15 mm was obtained. As the electroforming liquid, a nickel sulfamate electroforming liquid (NS160, manufactured by Showa Chemical Industry Co., LTD.) was used.

Example 1

Before the matrix was immersed in the electroforming liquid, a defoaming treatment was performed under the following conditions. The pretreated matrix was immersed in a pretreatment liquid stored in a pretreatment liquid tank and temperature-controlled at 25° C. As the pretreatment liquid, pure water was used. While pure water was being degassed at a treatment water amount of 5 L/min using a vacuum degassing device (water-based vacuum degassing device TKH-11, manufactured by Chiyoda Electric Co., Ltd.), ultrasound waves of a basic frequency of 35 kHz were applied to the recessed patterns of the matrix at an output of 600 W for 3 minutes. The dissolved oxygen concentration of the pure water was 1.0 mg/L or less.

The defoamed matrix was taken out from the pretreatment liquid tank and immersed in the electroforming liquid to perform an electroforming treatment according to the basic conditions.

Comparative Example 1

Before the matrix was immersed in the electroforming liquid, a defoaming treatment was performed under the following conditions. The pretreated matrix was immersed in pure water stored in a pretreatment liquid tank and temperature-controlled at 25° C. Ultrasound waves of a basic frequency of 35 kHz were applied to the recessed patterns of the matrix at an output of 600 W for 3 minutes. A degassing treatment using a vacuum degassing device was not performed unlike Example 1.

The defoamed matrix was taken out from the pretreatment liquid tank and immersed in the electroforming liquid to perform an electroforming treatment according to the basic conditions.

Comparative Example 2

An electroforming treatment was performed according to the basic conditions without performing a defoaming treatment.

(Results)

Figure 11:
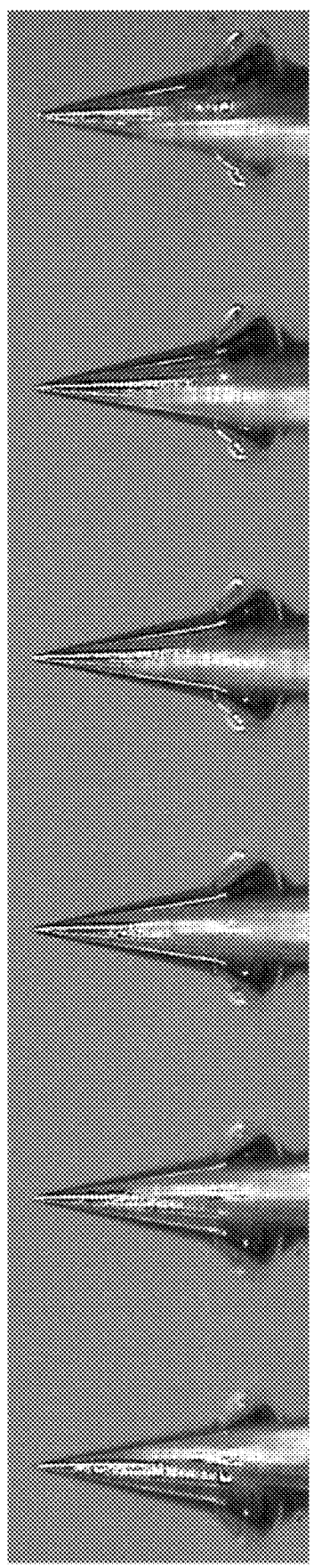
FIG. 11 is an external appearance image of a protruding pattern of an electroforming mold according to Example 1.
Figure 12:
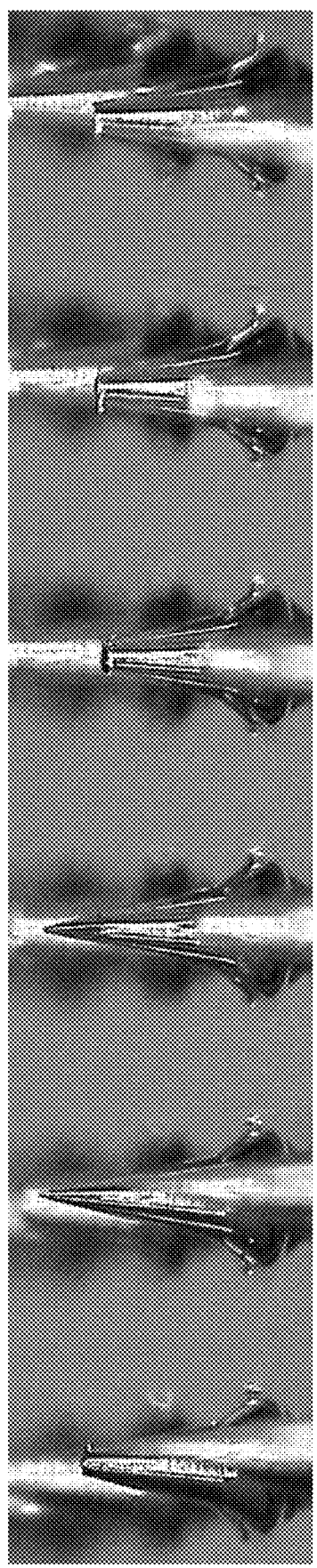
FIG. 12 is an external appearance image of a protruding pattern of an electroforming mold according to Comparative Example 1.
Figure 13:
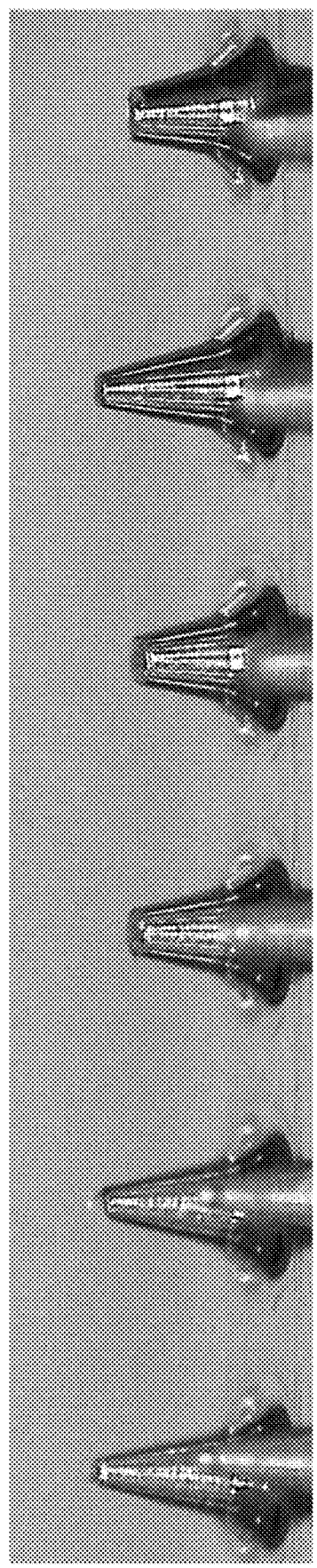
FIG. 13 is an external appearance image of a protruding pattern of an electroforming mold according to Comparative Example 2.

FIG. 11 is an external appearance image of a protruding pattern of an electroforming mold according to Example 1, FIG. 12 is an external appearance image of a protruding pattern of an electroforming mold according to Comparative Example 1, and FIG. 13 is external appearance image of a protruding pattern of an electroforming mold according to Comparative Example 2.

According to the external appearance image of the electroforming mold according to Example 1, cavities and/or defects were not observed in the protruding pattern. On the other hand, in Comparative Example 1, cavities and/or defects were observed in some protruding portions of the protruding pattern. In addition, in Comparative Example 2, cavities and/or defects were observed in a large number of protruding portions of the protruding pattern.

According to the example, before an electroforming treatment is performed, by immersing the matrix having the needle-like recessed patterns in the degassed pretreatment liquid and applying ultrasound waves to the recessed patterns, the recessed portions can be fully filled with the degassed pretreatment liquid. The use of the matrix having the needle-like recessed patterns fully filled with the degassed pretreatment liquid makes it possible to suppress the generation of cavities and/or defects in the electroforming mold.

Next, the transdermal absorption sheet was produced using the electroforming mold obtained from Example 1.

(Manufacturing of Mold)

On the electroforming mold obtained from Example 1, a film of silicone rubber (SILASTIC-MDX4-4210, manufactured by Dow Corning Corporation) having a thickness of 0.6 mm was formed. In a state in which the tip end portion of the electroforming mold was caused to protrude 50 μm from the film surface, the silicone rubber film was thermally cured. Next, the cured silicone rubber film was peeled off from the electroforming mold. A mold of a reversed article of silicone rubber having a through-hole having a diameter of about 30 μm was manufactured. The recessed patterns of 10 rows×10 columns arranged two-dimensionally were formed at the center portion of the mold. The surface with wide opening portions of the recessed patterns was set to the surface of the mold and the surface having a through-hole having a diameter of 30 μm (air vent hole) was set to the back surface of the mold.

(Preparation of Polymer Solution Including Drug)

Hydroxyethyl starch (manufactured by Fresenius Kabi AG) was dissolved in water to prepare an 8% aqueous solution. Next, 2% by mass of human serum albumin (manufactured by Wako Pure Chemical Industries, Ltd.) as a drug was added to the aqueous solution. The aqueous solution was used as a polymer solution containing a drug. After the solution was prepared, the solution was exposed under an environment of a reduced pressure of 3 kPa for 4 minutes and the polymer solution containing a drug (drug solution) was degassed.

(Preparation of Polymer Solution Not Containing Drug)

A 30% aqueous solution obtained by dissolving hydroxypropyl Cellulose (manufactured by Nippon Soda Co., Ltd.) in water was used as a polymer solution not containing a drug. After the solution was prepared, the solution was exposed under an environment of a reduced pressure of 3 kPa for 4 minutes and the polymer solution not containing a drug (base solution) was degassed.

(Drug Solution Filling Step and Drug Solution Drying Step)

The recessed patterns of the mold were filled with the drug solution using a drug solution filling device. The drug solution filling device includes a driving unit which has an X axis driving portion and a Z axis driving portion and controls relative position coordinates of a mold and a nozzle, a liquid supply device (Super small amount fixed-quantity dispenser SMP-III, manufactured by Musashi Engineering, Inc.) from which the nozzle is detachable, a suction base which fixes the mold, a laser displacement meter (HL-C201A, manufactured by Panasonic Corporation) which measures the shape of the mold surface, a load cell which measures nozzle pressing pressure (LCX-A-500N, manufactured by Kyowa Electronic Instruments Co., Ltd.), a control system which controls the Z axis based on the surface shape and the data of the value of measured pressing pressure, and a stainless steel nozzle which is attached to the liquid supply device.

A gas permeable film having one side of 15 mm (PORE-FLON FP-010, manufactured by Sumitomo Electric Industries, Ltd., POREFLON: registered trademark) was installed on the horizontal suction base and the mold was placed such that the surface was laid thereon. The pressure was reduced from the mold back surface direction with a suction pressure of a gauge pressure of 90 kPa to fix the gas permeable film and the mold onto the suction base.

While the nozzle was being pressed against the back surface of the mold using the Z axis driving portion and the nozzle was being moved using the X axis driving portion, the recessed patterns were filled with the drug solution from the nozzle. The mold after the filling with the drug solution was completed was left to stand under an environment at a temperature of 5° C. and a relative humidity of 50%RH for 30 minutes to dry the drug solution. The drug solution was localized at the tip ends of the recessed patterns by drying.

(Base Solution Filling Step and Base Solution Drying Step)

A thin stainless steel sheet having opening portions was prepared as a mold. The mold filled with the drug solution was fixed to the suction device by suction. The recessed patterns of the mold were aligned such that the recessed patterns were placed in the opening portions of the thin stainless steel sheet. The thin stainless steel sheet was superposed on the surface of the mold on which the recessed patterns were formed. The base solution was poured into the opening portion of the thin stainless steel sheet and the excessive base solution was scraped with a squeegee or a round bar. The recessed patterns were filled with the base solution.

Under an environment at a temperature of 23° C., a relative humidity of 45%RH, and a wind speed of 0.4 m/s, the mold was installed on a hot plate at 35° C. and left to stand for 6 hours to dry the solution. The moisture content of the base solution reached 5% or less.

(Peeling-Off Step)

The polymer sheet was peeled off from the mold by pulling up the polymer sheet while sucking air and thus a transdermal absorption sheet having protruding patterns having a three-dimensional arrangement structure and including a layer including the drug solution at the tip end and a layer not including the drug solution was produced.

(Shape of Transdermal Absorption Sheet)

No defect was observed in the protruding pattern of the transdermal absorption sheet. Cavities and/or defects were not generated in the electroforming mold manufactured in Example 1. Since a reverse type mold was manufactured using the electroforming mold and a transdermal absorption sheet was produced from the mold, no defect was observed in the protruding pattern. In addition, since the electroforming mold is used, the reverse type mold can be effectively manufactured and as a result, a transdermal absorption sheet can be effectively produced.

EXPLANATION OF REFERENCES

10: mold
10A: recessed pattern
10B: surface
12: recessed portion
14: thermoplastic resin
20: cathode
22: shaft
24: cathode plate
26: fixing member
30: pretreatment liquid tank
32: pretreatment liquid
34: circulation flow passage
36: vacuum degassing device
38: ultrasound oscillator
40: dissolve oxygen meter
50: mold
50A: recessed pattern
50B: surface
60: electroforming device
62, 62A: electroforming liquid
64: electroforming tank
66: drain tank
68: pellet
70: titanium case
72: drain pipe
74: supply pipe
80: metal body
82: electroforming mold
82A: protruding pattern
100: original plate
100A: protruding pattern
100B: flat surface
200: polymer solution
210: polymer sheet
220: transdermal absorption sheet
220A: protruding pattern
300: base material

What is claimed is:

1. A method of producing a transdermal absorption sheet, comprising:
   a preparation step of preparing a matrix having a needle-like recessed pattern;
   a filling step of immersing the matrix in a degassed pretreatment liquid stored in a pretreatment liquid tank and applying ultrasound waves generated from an ultrasound oscillator to the needle-like recessed pattern of the matrix to fill recessed portions constituting the needle-like recessed pattern with the pretreatment liquid;
   a taking-out step of taking out the matrix from the pretreatment liquid tank;
   a formation step of immersing the matrix in an electroforming liquid stored in an electroforming tank and performing an electroforming treatment to form a metal body on a surface of the matrix on which the needle-like recessed pattern is formed;
   a peeling-off step of peeling off the metal body from the matrix to obtain an electroforming mold having a protruding pattern having an inverted shape of the needle-like recessed pattern;
   a step of manufacturing a mold having the needle-like recessed pattern using the electroforming mold; and
   a step of filling the needle-like recessed pattern of the mold with a polymer solution including a drug and then drying the polymer solution to form a polymer sheet.

2. The method of producing the transdermal absorption sheet according to claim 1,
wherein the degassed pretreatment liquid is water.

3. The method of producing the transdermal absorption sheet according to claim 1,
wherein the ultrasound oscillator and the surface of the matrix on which the needle-like recessed pattern is formed are arranged to face each other.

4. The method of producing the transdermal absorption sheet according to claim 1,
wherein the matrix is formed of a resin material.

5. The method of producing the transdermal absorption sheet according to claim 4,
wherein the resin material is the thermoplastic resin or an ultraviolet curable resin.

6. The method of producing the transdermal absorption sheet according to claim 1,
wherein a dissolved oxygen concentration of the degassed pretreatment liquid is 0.5 mg/L or less.

7. The method of producing the transdermal absorption sheet according to claim 1, further comprising:
providing a vacuum degassing device which is connected to the pretreatment liquid tank via a circulation flow passage,
wherein the degassed pretreatment liquid is prepared by circulating a pretreatment liquid between the pretreatment liquid tank and the vacuum degassing device.

8. The method of producing the transdermal absorption sheet according to claim 1,
wherein the step of manufacturing the mold includes manufacturing a resin mold having the needle-like recessed pattern having an inverted shape of the protruding pattern of the electroforming mold.

9. The method of producing the transdermal absorption sheet according to claim 1, further comprising:
a peeling-off step of peeling off the polymer sheet from the mold.

10. The method of producing the transdermal absorption sheet according to claim 1,
wherein the polymer solution includes a water-soluble material.

* * * * *